(12) United States Patent
Shalaby

(10) Patent No.: US 6,498,229 B1
(45) Date of Patent: Dec. 24, 2002

(54) DIRECT SYNTHESIS OF SEGMENTED GLYCOLIDE COPOLYMERS AND CRYSTALLINE MATERIALS THEREFROM

(75) Inventor: Shalaby W. Shalaby, Anderson, SC (US)

(73) Assignee: Poly-Med, Inc., Anderson, SC (US)

( * ) Notice: Subject to any disclaimer, the term of this patent is extended or adjusted under 35 U.S.C. 154(b) by 0 days.

(21) Appl. No.: 09/946,430

(22) Filed: Sep. 5, 2001

(51) Int. Cl.$^7$ .......................... C08G 63/60; C08G 63/08
(52) U.S. Cl. ................. 528/302; 528/354; 528/357; 528/361; 525/437; 525/411; 606/77; 606/230
(58) Field of Search .................. 528/302, 354, 528/357, 361; 606/77, 230; 525/437, 411

(56) References Cited

U.S. PATENT DOCUMENTS

| | | | |
|---|---|---|---|
| 4,429,080 A | 1/1984 | Casey et al. ................. 525/415 |
| 4,470,416 A | * 9/1984 | Kafrawy et al. ......... 128/335.5 |
| 4,532,928 A | 8/1985 | Bezwada et al. ........ 128/335.5 |
| 4,543,952 A | 10/1985 | Shalaby ................... 128/335.5 |
| 5,133,739 A | * 7/1992 | Bezwada et al. ........... 606/230 |
| 5,236,444 A | 8/1993 | Muth et al. ................. 606/230 |
| 5,403,347 A | 4/1995 | Roby et al. ................. 606/230 |
| 5,431,679 A | 7/1995 | Bennett et al. ............. 606/230 |
| 5,468,253 A | 11/1995 | Bezwada et al. ........... 606/230 |
| 5,554,170 A | 9/1996 | Roby et al. ................. 606/230 |
| 5,644,002 A | 7/1997 | Cooper et al. .............. 525/411 |
| 5,713,920 A | 2/1998 | Bezwada et al. ........... 606/230 |
| 5,854,383 A | * 12/1998 | Erneta et al. ............. 528/354 |
| 6,206,908 B1 | 3/2001 | Roby ......................... 606/228 |
| 6,255,408 B1 | 7/2001 | Shalaby ..................... 525/437 |

OTHER PUBLICATIONS

Shalaby W. Shalaby and H.E. Blair. (1981). Chapter 3 of *Thermal Characterization of Polymeric Materials*. New York: Academic Press. p. 331.

Shalaby W. Shalaby and H.E. Blair. (1981). "Chapter 4" of *Thermal Characterization of Polymeric Materials*. New York: Academic Press. p. 402.

Mandelkern, Leo. *Crystallization of Polymers*. New York: McGraw Hill. pp. 105–106.

Correa, D.E. et al. (2000). Sixth World Biomaterials Congress, *Trans Soc. Biomat.*, II. 992.

* cited by examiner

*Primary Examiner*—Ana Woodward
(74) *Attorney, Agent, or Firm*—Leigh P. Gregory

(57) ABSTRACT

The present invention is directed to a method for the direct, one-step synthesis of crystalline segmented glycolide copolymers having less than 80 percent glycolide-based sequences in the copolyester chain. The copolyester chain can also be formed using a polyether glycol as the initiator for the ring-opening copolymerization of glycolide and other cyclic monomers to form highly hydrophilic materials.

16 Claims, No Drawings

DIRECT SYNTHESIS OF SEGMENTED GLYCOLIDE COPOLYMERS AND CRYSTALLINE MATERIALS THEREFROM

BACKGROUND OF THE INVENTION

Strategies for the synthesis of crystalline absorbable glycolide-based polymers based primarily on glycolide for the production of medical devices that exhibit in-use dimensional stability have been limited to (1) random copolymers with at least 80 percent of their chains derived from glycolide; or (2) segmented/block copolymers which are made by two-step synthesis entailing the preparation of a prepolymer containing a minor Traction of glycolate sequence, following end-grafting with glycolide or a mixture of monomers containing more than 80 percent glycolide. Composition limitations associated with the random copolymer approach and process complexity and fair-to-inadequate reproducibility encountered in the two-step synthesis of segmented glycolide copolymer provided the incentive to explore a simple, and yet reliable, approach to prepare crystalline glycolide copolymer with a broad range of physicochemical properties and possibly unique functional performance.

SUMMARY OF THE INVENTION

Accordingly, this invention deals with the direct, one-step copolymerization of glycolide with one or more cyclic monomers, such as lactide, 1,5-dioxepan-2-one, and preferably, trimethylene carbonate and/or caprolactone using low molecular weight monofunctional or difunctional alcohols, amines, or aminoalcohols as ring opening initiators to produce crystalline copolymers having less than 80 percent glycolide-based sequences in their chains. This invention also deals with the direct copolymerization of glycolide with trimethylene carbonate and/or caprolactone using high molecular weight mono- or di-functional polyalkylene oxide, wherein the initiating functionality is a hydroxylic and/or amino group, to produce crystalline polyether-ester block copolymers with a crystalline copolyester component comprising less than 80 percent glycolide-based sequences.

More specifically, the present invention is directed to a direct method for preparing a crystalline, segmented/block glycolide-based copolymer which involves the single step of heating a mixture of glycolide, a hydroxylic or amine initiator, an organo-metallic catalyst, and at least one further comonomer which is lactide, 1,5-dioxepan-2-one, trimethylene carbonate, caprolactone, or mixtures thereof, to a temperature in the range of from about 110° C. to about 180° C. Preferably, the molar ratio of glycolide to the at least one further comonomer is 80:20 or less. It is also preferred that the molar ratio of glycolide and the at least one further comonomer to catalyst is in the range of about 20,000:1 to about 90,000:1. Preferred initiators include 1,3-propanediol, trimethylol propane, and triethanolamine. In another embodiment, a preferred initiator is a difunctional polyalkylene oxide, preferably polyethylene glycol. For that embodiment it is preferred that the molar ratio of glycolide and the at least one further comonomer to the polyethylene glycol is in the range of from about 10:1 to about 1,000:1.

The present invention is also directed to a crystalline, segmented/block glycolide copolymer having less than about 80% by mole glycolide made by a direct method which involves the single step of heating a mixture of glycolide, an initiator, a catalyst, and at least one further comonomer which is lactide, 1,5-dioxepan-2-one, trimethylene carbonate, caprolactone, or mixtures thereof, to a temperature in the range of from about 110° C. to about 180° C. Preferably the at least one further comonomer is trimethylene carbonate, caprolactone, or mixtures thereof. A preferred end use for the crystalline, segmented/block glycolide copolymer of the present invention is as a molded or extruded medical device.

An alternative embodiment is directed to a crystalline, segmented/block copolymer which has a central block derived from a polyalkylene oxide, and end blocks which have less than about 80% by mole glycolide and at least about 20% by mole of a cyclic monomer which is lactide, 1,5-dioxepan-2-one, trimethylene carbonate, caprolactone, or mixtures thereof, made by a direct method which involves the single step of heating a mixture of glycolide, a functional polyalkylene oxide initiator, a catalyst, and at least one further comonomer which is lactide, 1,5-dioxepan-2-one, trimethylene carbonate, caprolactone, or mixtures thereof, to a temperature in the range of from about 110° C. to about 180° C. Preferably, the central block derived from a polyalkylene oxide comprises polyethylene glycol. Most preferably the polyethylene glycol block has a molecular weight of at least about 5,000 Dalton. One preferred end use for the crystalline copolymer of this embodiment of the present invention is as a hydrophilic medical device having finite solubility in water. Another preferred end use for the crystalline copolymer of this embodiment of the present invention is as a part of a controlled release system for bioactive agents. Yet another preferred end use for the crystalline copolymer of this embodiment of the present invention is as a molded or extruded medical device.

DETAILED DESCRIPTION OF PREFERRED EMBODIMENTS

This invention deals with the direct, one-step copolymerization of a monomer mixture containing less than 80 percent glycolide and the balance being one or more cyclic monomer such as lactide, 1,5-dioxepan-2-one, and preferably, trimethylene carbonate (TMC) and/or caprolactone (CL) using a mono- or di-functional diol, amine, or aminoalcohol, an organometallic catalyst, and the appropriate reaction temperature/time scheme to yield crystalline copolymers. In a preferred embodiment of this invention, a monomer mixture containing less than 80 percent glycolide and more than 20 percent TMC and/or CL is copolymerized in the presence of 1,3-propanediol, or trimethylol propane, or triethanolamine at a monomer to initiator ratio of 300 to 1500 and catalytic amounts of stannous octanoate at a monomer to catalyst ratio of 20,000 to 90,000. One aspect of this invention deals with the direct, one-step synthesis of crystalline, segmented copolymer containing less than 80 percent glycolide-based chain sequences that melt between 150° C. and 220° C. and a crystalline fraction exhibiting a heat of fusion of 20–90 J/g. Another aspect of this invention deals with extrusion of a typical copolymer, having about 70 to 79 percent glycolide-based repeat units, into a monofilament which can be further oriented into suture strands. Another aspect of this invention deals with conversion of a typical copolymer having about 60 and 70 percent of glycolide-based repeat units into molded articles, including connecting tubes or catheters, for use in conjunction with devices applicable in the ophthalmology, orthopedic, cardiovascular, and dialysis areas.

This invention also deals with the direct, one-step copolymerization of a monomer mixture containing less than 80 percent glycolide and the balance being TMC and/or CL using a high molecular weight mono- or di-functional polyalkylene oxide as the ring-opening polymerization initiator, wherein the initiating functionality is a hydroxylic and/or amino group, to produce a crystalline polyether-ester block copolymer with a crystalline copolyester component comprising less than 80 percent glycolide-based sequences. In a preferred embodiment of this invention, a monomer mixture containing less than 80 percent glycolide and more than 20 percent TMC and/or CL is copolymerized in the presence of polyethylene glycol to produce a hydrophilic crystalline copolyether-ester. In a more preferred embodiment a polyethylene glycol, having a molecular weight of more than 5 kDa, is used as the initiator to produce highly hydrophilic copolymer that may have a discernable solubility in water. These copolymers can be used to produce controlled drug delivery systems or can be melt processed by molding or extrusion into absorbable medical devices or a component thereof with unique physicochemical and biological properties. Medical devices based on these polyether-esters can be used in orthopedic, ophthalmic, and cardiovascular devices as well as controlled release systems for bioactive agents or scaffolds for tissue engineering. Further embodiment of the invention can be illustrated by, but not limited to, the examples described below.

EXAMPLE 1

Direct Synthesis of Segmented 70/30 Glycolide/Caprolactone Copolymer

In a predried reactor equipped for mechanical stirring, a mixture of preweighed initiator (1,3 propanediol, 0.146 g), glycolide (0.91 mole, 105.5 g), caprolactone (0.39 mole, 44.5 g), and a 0.2 M solution of stannous octanoate in toluene (to provide a monomer to catalyst molar ratio of 60,000) were charged under a nitrogen atmosphere. The mixture was redried under reduced purging with nitrogen, the polymerization charge was heated under dry nitrogen at 110° C. until all components melted. At this point, the temperature was raised to 180° C. (in about 30 minutes). The polymerization was allowed to continue until the product commenced to solidify, and then stirring was discontinued. The polymerization was allowed to continue to achieve a total polymerization time at 180° C. of 6 hours. At the conclusion of the polymerization, the product was cooled to room temperature, quenched with liquid nitrogen, isolated, and ground. The ground polymer was dried under reduced pressure at 25° C., 40° C., and then 80° C. The dried polymer was characterized for (1) melting temperature ($T_m$) and heat of fusion ($\Delta H$) using differential scanning calorimetry; (2) molecular weight in terms of inherent viscosity in hexafluoro isopropyl alcohol; and (3) infrared (as a thin film) and NMR (as a solution in deuterated hexafluoro-acetone) for composition. The relevant characterization data are summarized in Table I.

EXAMPLES 2–7

Preparation and Properties of Six Additional Copolymers

The method of Example 1 was applied to produce six additional copolymers. Specific data pertinent to the polymerization scheme and polymer properties are outlined in Table I.

EXAMPLE 8

Extrusion of Copolymer Orientation of Extrudates and Fiber Physical Properties

A number of dried polymers from Examples 1–7 were extruded at 220–235° C. using a single-screw extruder. The extrudates were oriented by drawing at 90–110° C. The tensile properties of representative fibers are summarized in Table II.

TABLE I

Glycolide/Caprolactone Copolymers: Synthesis & Properties

| | | Monomer (M) Charge | | Initiator | | Reaction Conditions[a] | | Polymer Properties | | |
|---|---|---|---|---|---|---|---|---|---|---|
| Example No. | Polymer Composition | Glycolide, Mole (g) | Caprolactone, Mole (g) | Type[b] | Weight (g) | Temp, °C. | Time, Hours | Tm, °C. | ΔH, J/g | Viscosity, dL/g |
| 1 | C/CL: 70/30 | 0.91 (105.5) | 0.39 (44.5) | A | 0.146 | 180 | 6 | 218 | 76.2 | 0.89 |
| 2 | G/CL: 60/40 | 0.7759 (90) | 0.5263 (60) | A | 0.327 | 180 | 6 | 157 | 22.1 | 0.62 |
| 3 | G/CL: 70/30 | 0.9052 (105.2) | 0.3947 (45) | B | 0.581 | 228 | 4.5 | 207 | 33 | 0.76 |
| 4 | G/CL: 70/30 | 0.9052 (105) | 0.3947 (45) | A | 0.327 | 180 | 6 | 209 | 66.9 | 0.74 |
| 5 | G/CL: 70/30 | 0.91 (105.5) | 0.39 (44.5) | A | 0.198 | 180 | 6 | 204 | 43.9 | 0.82 |
| 6 | G/CL: 70/30 | 0.91 (105.5) | 0.39 (44.5) | A | 0.151 | 180 | 2 | 199 | 140 | 0.69 |
| 7 | G/CL: 75/25 | 1.948 (226) | 0.649 (74) | A | 0.282 | 180 | 3 | 204 | 82.8 | 1.12 |

[a]A 0.2 M solution of stannous octanoate in toluene was used to provide a mole ratio of 60,000 for monomer/catalyst.
[b]A = 1,3 propane diol; B = trimethylolpropane.

TABLE II

Typical Fiber Properties of Glycolide/Caprolactone Copolymers

| Using Polymer From Example | Diameter, mm | Elongation, % | Tensile Strength Kpsi | Modulus, Kpsi |
|---|---|---|---|---|
| 1 | 10.6 | 43 | 70 | 160 |
| 7 | 16.6 | 44 | 83 | 290 |

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicants hereby disclose all subranges of all ranges disclosed herein. These subranges are also useful in carrying out the present invention.

What is claimed is:

1. A direct method for preparing a crystalline, segmented/block glycolide-based copolymer comprising the single step of:

heating a mixture of glycolide, a hydroxylic or amine initiator, an organo-metallic catalyst, and at least one further comonomer selected from the group consisting of lactide, trimethylene carbonate, caprolactone, and mixtures thereof, to a temperature in the range of from about 110° C. to about 180° C.

2. The method set forth in claim 1 wherein the glycolide-based copolymer comprises 80% by mole or less of glycolide-derived units and 20% by mole or more of units derived from the at least one further comonomer.

3. The method set forth in claim 1 wherein the molar ratio of glycolide and the at least one further comonomer to catalyst is in the range of about 20,000:1 to about 90,000:1.

4. The method set forth in claim 1 wherein the initiator is selected from the group consisting of 1,3-propanediol, trimethylol propane, and triethanolamine.

5. The method set forth in claim 1 wherein the initiator comprises a difunctional polyalkylene oxide.

6. The method set forth in claim 5 wherein the initiator comprises polyethylene glycol.

7. The method set forth in claim 6 wherein the molar ratio of glycolide and the at least one further comonomer to the polyethylene glycol is in the range of from about 10:1 to about 1,000:1.

8. A crystalline, segmented/block copolymer having less than about 80% by mole glycolide made by a direct method comprising a single step comprising:

heating a mixture of glycolide, a hydroxylic or amine initiator, an organo-metallic catalyst, and at least one further comonomer selected from the group consisting of lactide, trimethylene carbonate, caprolactone, and mixtures thereof, to a temperature in the range of from about 110° C. to about 180° C.

9. The crystalline copolymer set forth in claim 8 wherein the at least one further comonomer is selected from the group consisting of trimethylene carbonate, caprolactone, and mixtures thereof.

10. The crystalline copolymer set forth in claim 8 comprising a molded or extruded medical device.

11. A crystalline, segmented/block copolymer having:

a central block derived from a polyalkylene oxide; and end blocks comprising less than about 80% by mole glycolide and at least about 20% by mole of a cyclic monomer selected from the group consisting of lactide, trimethylene carbonate, caprolactone, and mixtures thereof, made by a direct method comprising a single step comprising:

heating a mixture of glycolide, a functional polyalkylene oxide initiator, a catalyst, and at least one further comonomer selected from the group consisting of lactide, trimethylene carbonate, caprolactone, and mixtures thereof, to a temperature in the range of from about 110° C. to about 180° C.

12. The crystalline copolymer set forth in claim 11 wherein the central block derived from a polyalkylene oxide comprises polyethylene glycol.

13. The crystalline copolymer set forth in claim 12 wherein the polyethylene glycol block has a molecular weight of at least about 5,000 Dalton.

14. The crystalline copolymer set forth in claim 13 comprising a hydrophilic medical device having finite solubility in water.

15. The crystalline copolymer set forth in claim 13 comprising a part of a controlled release system for bioactive agents.

16. The crystalline copolymer set forth in claim 11 comprising a molded or extruded medical device.

\* \* \* \* \*